US00PP26352P2

(12) United States Plant Patent
Saul

(10) Patent No.: US PP26,352 P2
(45) Date of Patent: Jan. 26, 2016

(54) ***PHLOX* PLANT NAMED 'JORDAN SCHUSTER'**

(50) Latin Name: *Phlox paniculata*
Varietal Denomination: Jordan Schuster

(71) Applicant: Richard G. Saul, Cleveland, GA (US)

(72) Inventor: Richard G. Saul, Cleveland, GA (US)

(73) Assignee: ITSAUL PLANTS LLC, Alpharetta, GA (US)

( * ) Notice: Subject to any disclaimer, the term of this patent is extended or adjusted under 35 U.S.C. 154(b) by 203 days.

(21) Appl. No.: 13/998,487

(22) Filed: Nov. 5, 2013

(51) Int. Cl.
*A01H 5/02* (2006.01)

(52) U.S. Cl.
USPC ..... Plt./320

(58) Field of Classification Search
USPC ..... Plt./320
See application file for complete search history.

*Primary Examiner* — Anne Grunberg
(74) *Attorney, Agent, or Firm* — Penny J. Aguirre

(57) ABSTRACT

A new cultivar of *Phlox*, 'Jordan Schuster', characterized by its fragrant, bright pink flowers with diffused dark pink eyes that radiate outwardly especially on the top side of the petals, its pointed, triangular shaped terminal panicles, its very uniform lateral branching with lower lateral branches forming more typical rounded cymes that emerge while the terminal panicles are still in color to form a large mass of flowers and the lateral cymes continue to bloom throughout the summer, its medium green foliage that has good resistance to powdery mildew, and its compact growth habit.

2 Drawing Sheets

Botanical classification: *Phlox paniculata.*
Cultivar designation: 'Jordan Schuster'.

BACKGROUND OF THE INVENTION

The present invention relates to a new and distinct cultivar of *Phlox paniculata* and will be referred to hereafter by its cultivar name, 'Jordan Schuster'. 'Jordan Schuster' represents a new herbaceous perennial grown for landscape use.

The Inventor discovered the new cultivar in July 2007 as a naturally occurring branch mutation of *Phlox* 'Bright Eyes' (not patented) in a container in a production block at his nursery in Dahlonega, Ga.

Asexual propagation of the new cultivar was first accomplished by stem cuttings by the Inventor in 2009 in Dahlonega, Ga., USA. Asexual propagation by stem cuttings and root cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Jordan Schuster' as a unique cultivar of *Phlox*.

1. 'Jordan Schuster' exhibits fragrant, bright pink flowers with diffused dark pink eyes that radiate outwardly especially on the top side of the petals.
2. 'Jordan Schuster' exhibits pointed, triangular shaped terminal panicles.
3. 'Jordan Schuster' exhibits very uniform lateral branching with lower lateral branches forming more typical rounded cymes that emerge while the terminal panicles are still in color to form a large mass of flowers and the lateral cymes continue to bloom throughout the summer.

4. 'Jordan Schuster' exhibits medium green foliage that has good resistance to powdery mildew.
5. 'Jordan Schuster' exhibits a compact growth habit reaching a height of 46 to 66 cm.

The parent of 'Jordan Schuster', 'Bright Eyes', differs from 'Jordan Schuster' in being taller in height, in having looser, more round terminal panicles, and in having petals that are lighter in color with lighter colored eyes. 'Jordan Schuster' can be most closely compared to the *Phlox* cultivars 'Cotton Candy' (U.S. Plant Pat. No. 13,420) and 'Peppermint Twist' (U.S. Plant Pat. No. 18,196). 'Cotton Candy' is similar to 'Jordan Schuster' in being resistant to powdery mildew. 'Cotton Candy' differs from 'Jordan Schuster' in having lighter pink flowers with darker, more compact eyes, in having flatter, broader petals with more rounded apices, in having no space between the petals at the outer margin of the flowers, in having darker stems, and in having new growth tips that are more red in color. 'Peppermint Twist' is similar to 'Jordan Schuster' in plant height and in having large flower heads. 'Peppermint Twist' differs from 'Jordan Schuster' in having a pink strip that radiates through the center of each petal and in having rounded petals that lay flatter with no space in between them.

BRIEF DESCRIPTION OF THE DRAWING

The accompanying colored photographs illustrate the overall appearance and distinct characteristics of the new *Phlox*. The photographs were taken of one year-old plants of 'Jordan Schuster' as grown outdoors in containers in Dahlonega, Ga.

The photograph (in a two-gallon container) in FIG. 1 provides a side view of a plant of 'Jordan Schuster' in bloom and shows the lateral cymes blooming with the terminal panicles.

Figure 1:
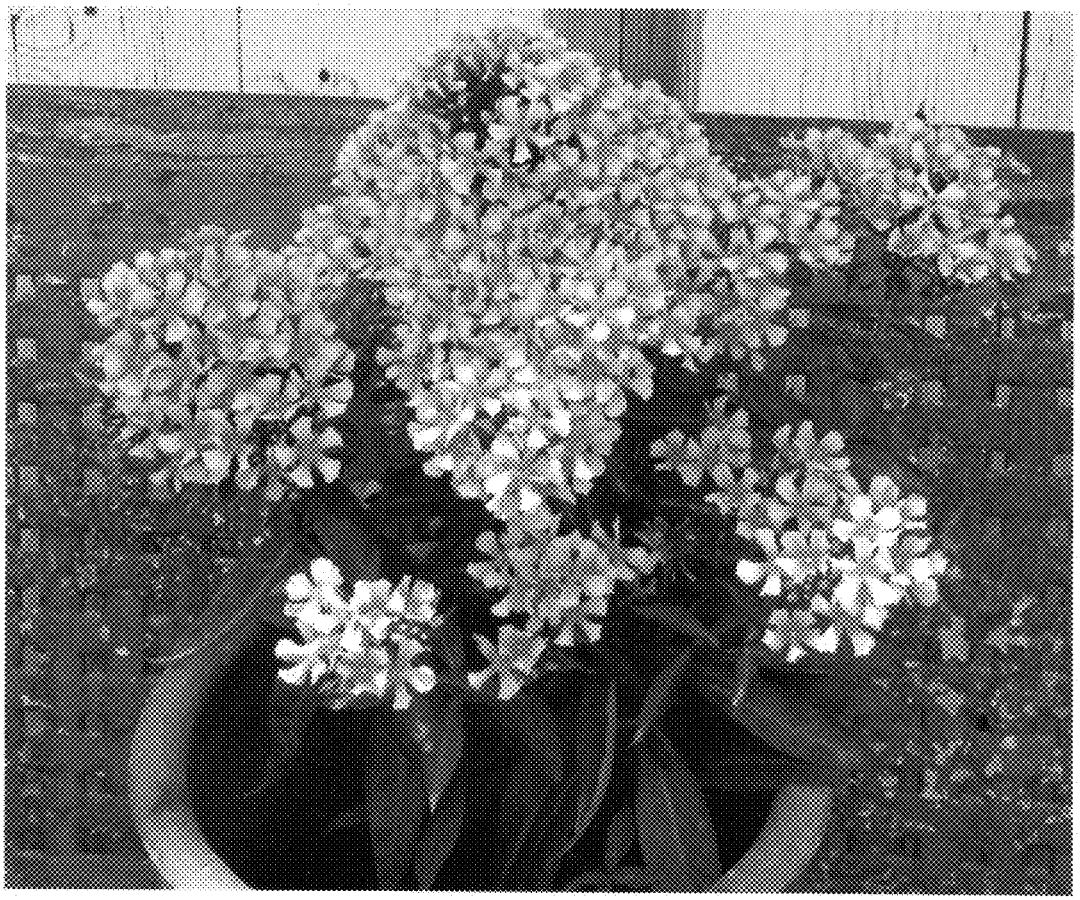
Figure 2:
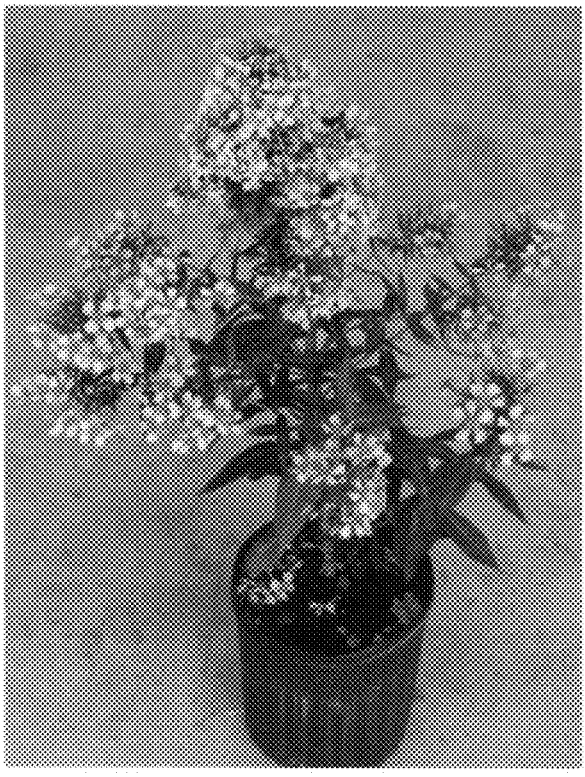

The photograph (in a one-gallon container) in FIG. 2 provides a view of the lateral branching of 'Jordan Schuster'.

Figure 3:
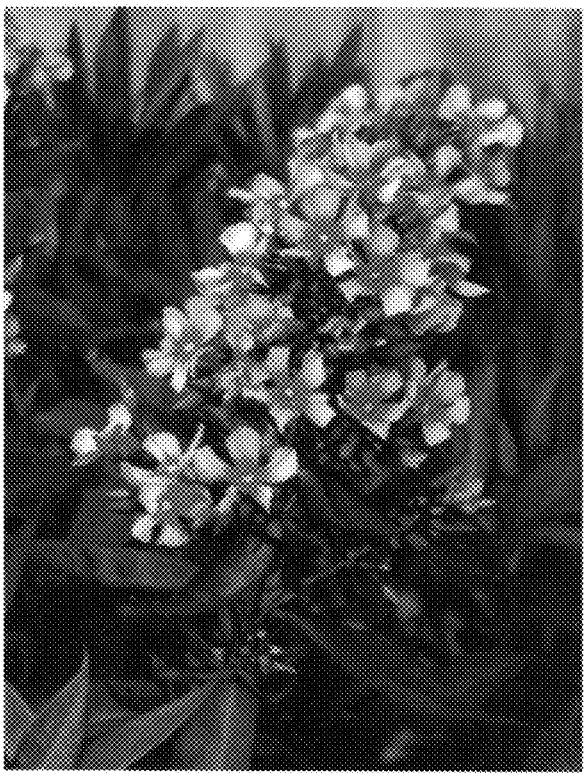

The photograph in FIG. 3 provides a close-up view of a terminal panicle of 'Jordan Schuster'.

The colors in the photographs may differ slightly from the color values cited in the detailed botanical description, which accurately describe the colors of the new *Phlox*.

DETAILED BOTANICAL DESCRIPTION OF THE PLANT

The following is a detailed description of a one year-old plants of the new cultivar as grown outdoors in a one-gallon in Dahlonega, Ga. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—July to August in Dahlonega, Ga.

*Plant habit.*—Herbaceous perennial, compact.

*Height and spread.*—Reaches 4.6 to 66 cm in height in bloom and about 40 cm in spread.

*Hardiness.*—At least hardy in U.S.D.A. Zones 5 to 8.

*Diseases and pests.*—Has been shown to have good resistant to powdery mildew.

*Root description.*—Fibrous and fine.

*Growth rate.*—Moderate.

*Propagation.*—Stem or root cuttings.

Stem description:

*Stem size.*—Main stem, an average of 30 cm in length and 1.5 cm in width, lateral stems; variable, up to 30 cm in length and 3 mm in width.

*Stem shape.*—Oval.

*Stem strength.*—Strong and sturdy.

*Stem color.*—Mature; a blend of 145A and 146C, young; 146A.

*Stem surface.*—Glabrous, slightly glossy.

*Stem aspect.*—Held nearly upright.

*Internode length.*—Up to 2 cm.

*Branching habit.*—An average 3 main stems, an average of 6 lateral branches per main stem.

Foliage description:

*Leaf shape.*—Narrowly elliptic.

*Leaf division.*—Simple.

*Leaf base.*—Attenuate.

*Leaf apex.*—Acuminate.

*Leaf venation.*—Pinnate, not conspicuous, matches leaf color on upper and lower surface.

*Leaf margins.*—Entire.

*Leaf attachment.*—Sessile.

*Leaf arrangement.*—Opposite.

*Leaf surface.*—Glabrous and dull on upper and lower surface.

*Leaf color.*—Young and mature upper surface; N137A, young and mature lower surface; 138B.

*Leaf size.*—An average of 7 cm in length and 1.5 cm in width.

*Leaf quantity.*—An average of 16.

*Leaf fragrance.*—None.

Flower description:

*Inflorescence type.*—Compound panicle on terminus of main stems with rounded cymes on the lateral branches.

*Lastingness of inflorescence.*—About 3 to 4 weeks from the opening of the first flower to senescence of last flower, individual flower lasts about 5 days, inflorescences on lateral blooms commence while the terminal panicle is in color and then continue to bloom.

*Inflorescence size.*—An average of 9 cm in height and 8 cm in diameter for terminal inflorescences, laterals are slightly smaller with fewer flowers.

*Flower fragrance.*—Sweet *phlox* fragrance.

*Flower number.*—Average of 40 per terminal inflorescence, and 8 per lateral stems.

*Flower aspect.*—Upright to outward, dependant on location on the inflorescence.

*Flower bud.*—An average of 7 mm in length and up to 4 mm in width, apex is conical in shape with base linear (tube portion), 145C in color.

*Flower form.*—Explanate with tubular base.

*Flower size.*—An average of 2 cm in length and 2.5 cm in width.

*Corolla tube.*—About 1.5 cm in length, 2 mm in width, color matches corolla lobe coloration on outer (same as lower surface of lobes) and inner surfaces (same as upper surface of lobes), glabrous and satiny on both surfaces.

*Corolla lobes.*—5, orbicular-obovate in shape, held nearly horizontally when fully open, slightly overlapping, about 1 cm in length and 0.8 cm in width, apex rounded, base broadly cuneate and fused to tube, entire margins, upper surface color when opening and mature base N74A, blending out and becoming a blend of 68B and 69B and 69D, lower surface color when first opening and maturing a blend of 70B and 69D, glabrous and satiny on both surfaces.

*Calyx.*—Campanulate in form comprised of fused sepals with lanceolate shaped sepal tips free, an average of 1 cm in length and 3 mm in width.

*Sepals.*—5, primarily fused with free tips, linear in shape, margins entire, base fused (about 80%), apex narrowly apiculate, an average of 0.5 cm in length and 1 mm in width, inner and outer surface is dull and slightly puberulent, color on outer surface; base is 145A, blending with N187A at the mid section to tip, color on inner surface is a blend of 141A and 142A.

*Peduncles.*—Oval in shape, primary an average of 2.5 cm in length and 3 mm in width, secondary an average of 1.5 cm in length and 2 mm in width, primary held upright, secondary held at about a 45° angle, glabrous and satiny surface, color is 146A.

*Pedicels.*—Oval in shape, an average of 5 mm in length and 1 mm in width, glabrous surface, color is 146A.

Reproductive organs:

*Gynoecium.*—1 pistil, stigma has 3 branches about 1 mm in length and 145C in color, style is about 1.5 cm in length, very fine and 145B in color, ovary is inferior, oblong in shape, about 2 mm in length and 1 mm in width and 145A in color.

*Androcoecium.*—5 stamens, anthers are basifixed, oblong in shape, 2 mm in length and varies between 10A and 11D in color, filaments are adnate to petals, 1 cm in length and NN155A in color, pollen was not observed.

*Seeds.*—Seed production has not been observed.

It is claimed:

1. A new and distinct cultivar of *Phlox* plant named 'Jordan Schuster' as herein illustrated and described.

* * * * *